United States Patent [19]

Ahmadi et al.

[11] Patent Number: 4,602,911
[45] Date of Patent: Jul. 29, 1986

[54] ADJUSTABLE RINGPROSTHESIS

[75] Inventors: Ali Ahmadi, Denzlingen, Fed. Rep. of Germany; Henri Moll, Bienne, Switzerland

[73] Assignee: General Resorts S.A., Bienne, Switzerland; by Henri Moll

[21] Appl. No.: 694,928

[22] Filed: Jan. 25, 1985

[30] Foreign Application Priority Data

Feb. 23, 1984 [DE] Fed. Rep. of Germany ....... 3406469

[51] Int. Cl.$^4$ .............................................. A61F 2/24
[52] U.S. Cl. ..................................................... 623/2
[58] Field of Search ................ 24/274 R, 279, 20 TT, 24/20 LS, 284, 483; 3/1.5; 128/346, 92 R, 92 EA

[56] References Cited

U.S. PATENT DOCUMENTS 3,840,018 10/1974 Heifetz ............................... 24/274 R
4,042,979 8/1977 Angell ........................................ 3/1.5
4,473,928 10/1984 Johnson .................................. 24/483

FOREIGN PATENT DOCUMENTS 3230858 3/1984 Fed. Rep. of Germany .

Primary Examiner—Vincent Millin
Assistant Examiner—James Prizant
Attorney, Agent, or Firm—Frishauf, Holtz, Goodman & Woodward

[57] ABSTRACT

An adjustable ringprosthesis designed particularly for being sewed onto the ring of the mitral valve or tricuspidal valve of a living heart uses a spring ribbon coiled with an overlap of about a half turn covered in a woven, braided or knitted cuff of a suitable synthetic fiber that can be sewed into place. An adjusting device (40) is fixedly positioned on a portion of the spring ribbon which is internally overlapped by an end portion which carries teeth so as to form a rack which can be driven by a screw (15) in the adjusting device for varying the diameter of the ring. The adjusting device is operated by an adjusting tool, the front end of which is guided into a screw-head socket (50) for turning the screw to change the ring diameter. The shaft of the tool is guided by a tube through a connecting piece (51) onto which the guide tube is screwed, and from which it can be unscrewed and removed when there is no further need for post-operative adjustment of the prosthesis.

11 Claims, 17 Drawing Figures

ADJUSTABLE RINGPROSTHESIS

The invention concerns an adjustable ringprosthesis for surgical correction of heart valve malfunction or for constricting the pulmonary artery, having a synthetic fabric cuff capable of being sewn into the heart valve ring of the mitral or the tricuspidal valve of the heart, wherein a spring ribbon coiled to form a ring is provided which has an end coiled internally in the ring that is circumferentially shiftable by means of an adjusting device mounted on the externally coiled part of the ribbon, into which device the forward end of an adjusting tool can be inserted and in which device the internally coiled end of the spring ribbon, having a toothed edge, engages into the threads of a screw which is turnable by the adjusting tool and is rotatably held in a guiding body having a slotted foot and a guide orifice.

A previous adjustable ring prosthesis of the kind just mentioned invented by the present applicants is disclosed in German Pat. No. No. P 32 30 858.2-35 granted Aug. 16, 1984. The screw of the adjusting device in the adjustable ringprosthesis according to that previous device is disposed in a guide body open at one end and supported against a support tab protruding externally of the guide body and welded to the spring ribbon. Experiments under test conditions show that under unfavorable circumstances the screw can shift somewhat rearwardly and thereby jam. It further appeared that stresses could arise in the ring from the beating of the heart, which stresses produce torsion effects in a flexible adjusting tool or screwdriver to such an extent that unimpaired adjustment operation is no longer assured.

SUMMARY OF THE INVENTION

The object of the invention is to provide a ringprosthesis of the above-described kind which is improved so that accurate and troublefree adjustment without danger of jamming of the adjustment device is obtainable, even in the presence of high stresses in the ring.

Briefly, the guide body has a coupling piece at its insertion opening for coupling on a guide tube or pipe for the introduction of the adjusting tool and a thrust bearing for the screw is provided in the guide body at its side opposite the insertion opening.

Because the screw is enclosed on all sides in the guide body, it cannot jam against the ring even under the strongest pulling forces applied by the screwdriver. The coupling piece on the guide body permits the coupling on of a flexible guide tube through which a rotation-stiff screwdriver can be introduced, even after the implantation of the ringprosthesis. The flexible guide tube lays itself lightly on the heart and can lead to the outside at a suitable place. When a new adjustment is necessary, the stiff screwdriver which is insensitive with regard to torsion can be inserted through the guide tube right up to the screw and then actuated. Thereafter, the screwdriver is removed, while the guide tube can well remain in place. This procedure can be repeated as often as desired. Finally, the guide tube can be unscrewed in a simple way from the connection piece and then removed.

The coupling piece preferably is provided with external threading for attaching the guiding tube. The guide structure on which the coupling piece is provided can advantageously include a cylindrical body with an eccentrically disposed cavity for the screw, with a longitudinal slot where this location of the eccentric hole makes the wall thickest. It can also advantageously have a ring bead protruding at one end against which a surrounding shell lies. The cylindrical body can then be pushed into place with its slot against the spring ribbon and held on the spring ribbon by means of the shell just mentioned and two laterally disposed positioning plates affixed on the ring.

The ring ribbon itself can have portions of different flexibility, so that as it is adjusted with the adjusting tool, a deformation away from circularity can be produced.

BRIEF DESCRIPTION OF THE DRAWINGS

The invention is further described by way of illustrative example with reference to the annexed drawing, in which.

DESCRIPTION OF THE ILLUSTRATED EMBODIMENT

Figure 1:
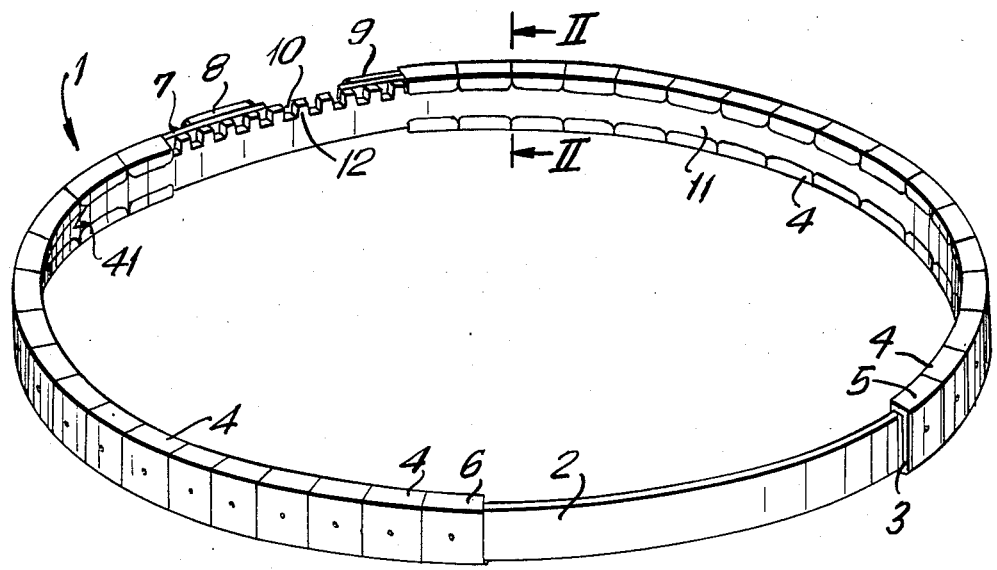
FIG. 1 is a perspective view of a ring of the ringprosthesis according to the invention shown with the fabric sleeve and the screw guide structure both removed.
Figure 3:
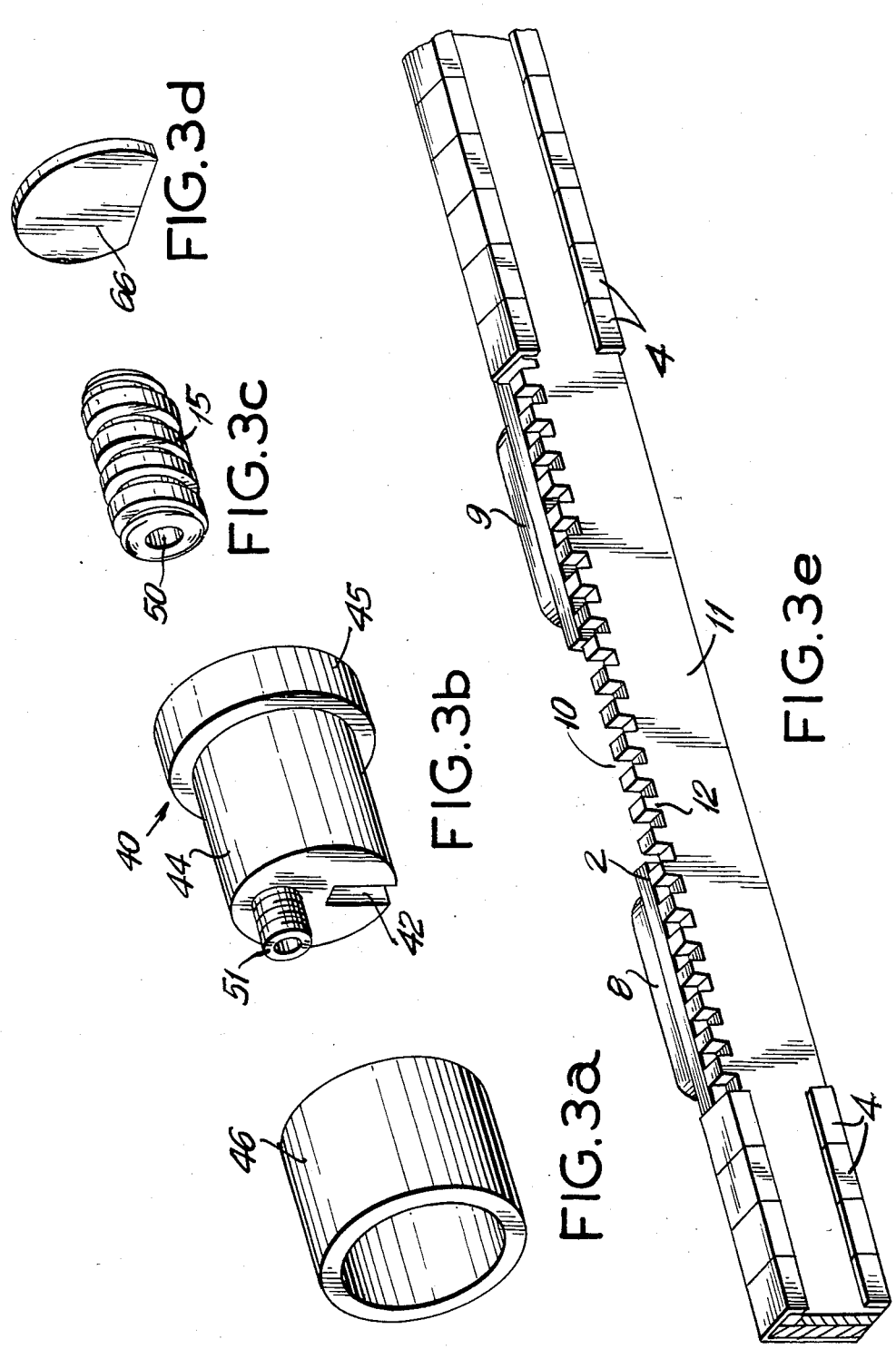
FIGS. 3a, 3b, 3c, 3d and 3e are perspective views in exploded arrangement illustrating, respectively, the toothed portion of the spring ribbon of the ringprosthesis, the shell or sleeve for the screw guide, the slotted guide body with its connecting piece on one end and its protruding bead or flange on the other, the screw by which adjustment is made and, finally, the plate that provides the rear bearing surface for the screw.

FIG. 1 shows the adjustable ringprosthesis without the screw guide 40 of the adjusting device for it and other elements shown in FIG. 3 and also without the surrounding woven, plaited, or knitted tubular sleeve or cuff of synthetic resin material. The ring, designated as a whole with the reference numeral 1, consists of a ring-shaped partly coiled spring ribbon 2. The latter is provided with protective clasps externally spot-welded thereto, beginning with the extremity 3 of the outer end of the coil and extending over a considerable portion of the ring. In FIG. 1 the first protective clasp is designated 5 and the last protective clasp 6.

Figure 5:
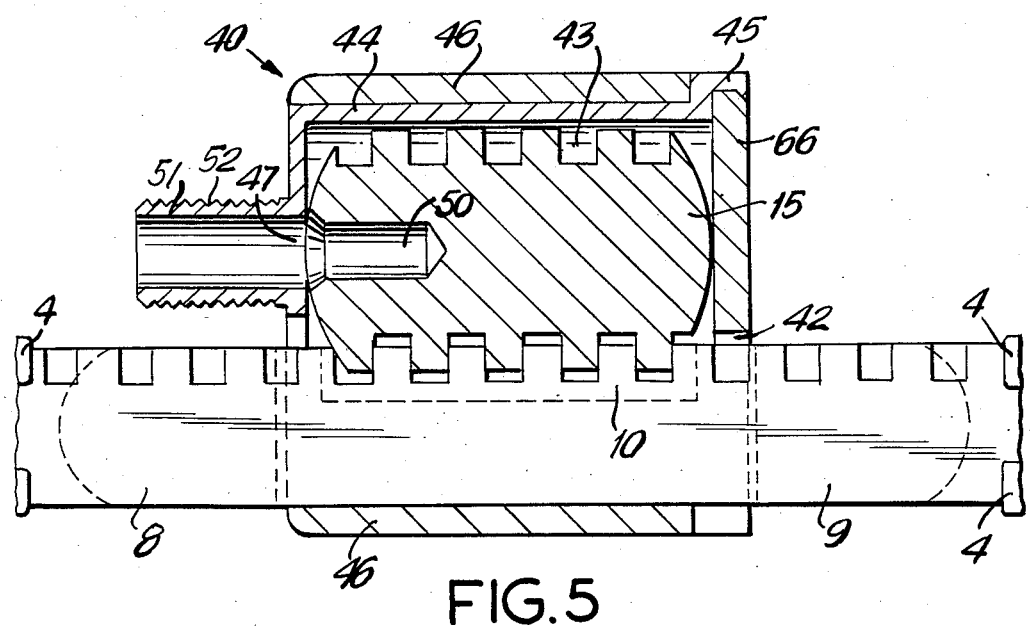
FIG. 5 is a longitudinal cross-section of the adjusting device with a side view of a portion of the spring ribbon passing therethrough.

As can be seen from FIGS. 1, 3 and 5 (FIG. 3 referring to the various FIGS. 3a, 3b . . . 3d), there is a region 7 free of protective clasps more or less in the middle of the first section of the ring beginning with the first protective clasp 5 and ending with the last protective clasp 6. In the region 7 there are externally applied stop straps or plates 8 and 9. Between the stop plates 8 and 9 a cut-out 10 is provided in the spring ribbon or strip 2, so that the width of the spring ribbon 2 is reduced in the region of this cut-out 10.

At the last protective clasp 6, a second section 11 of the spring ribbon 2 begins. The second section 11 of the spring ribbon 2 has essentially the same length as the first section provided with the protective clasps 4. This second section continues within the clasps 4 interiorly of the ribbon 2 to end at a point 41. Its edge shown as the upper edge in FIG. 1 is provided with crenellations or teeth 12 in a region near its end 41. The crenellation 2 extends over more or less a quarter of the entire length of the spring strip 2, which is to say over about half of the second section 11 of the spring ribbon 2. As shown in the drawing, the teeth 12 are preferably of rectangular meander shape, but since this portion of the ribbon forms a rack as further explained below, other toothing profiles are usable.

Figure 2:
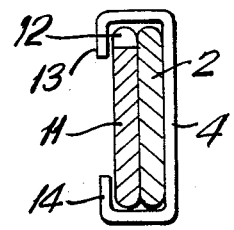
FIG. 2 is a cross-section along the line II—II of FIG. 1, on an enlarged scale.

The second section 11 of the spring ribbon 2, as shown in FIGS. 1 and 2, is coiled into the first section to form a partial overlap. For this purpose, it is guided into the bent-over ends 13 and 14 of the U-shaped protective clasps 4. The latter extend with their bent-over ends 13 and 14 far enough into the interior of the ring 1 for the second section 11 of the spring ribbon to be displaceably guided therein.

In the coiled state of the spring ribbon, the toothing 12 projects above the cut-out 10 of the first section of the spring ribbon to such an extent that it can engage a screw 15 which is rotatably held in a screw guide structure 40. By rotation of the screw 15, the second section 11 of the spring ribbon 2 carrying the toothing 12 is displaced so that this second section 11 is drawn more or less far inside the first second to which the protective clasps 4 are spot welded. In this manner the diameter of the ring 1 can be correspondingly varied.

Although the ring 1 is shown as circular in FIG. 1, it can, however, have various shapes. In particular, it can be circular, oval or kidney-shaped. The various shapes are obtained by providing different flexibility for various sections of the spring ribbon 2. When the ring 1 is narrowed or widened by actuation of the screw 5, the various segments of the ring 1 would then be deformed according to their respective flexibilities.

Figure 11:
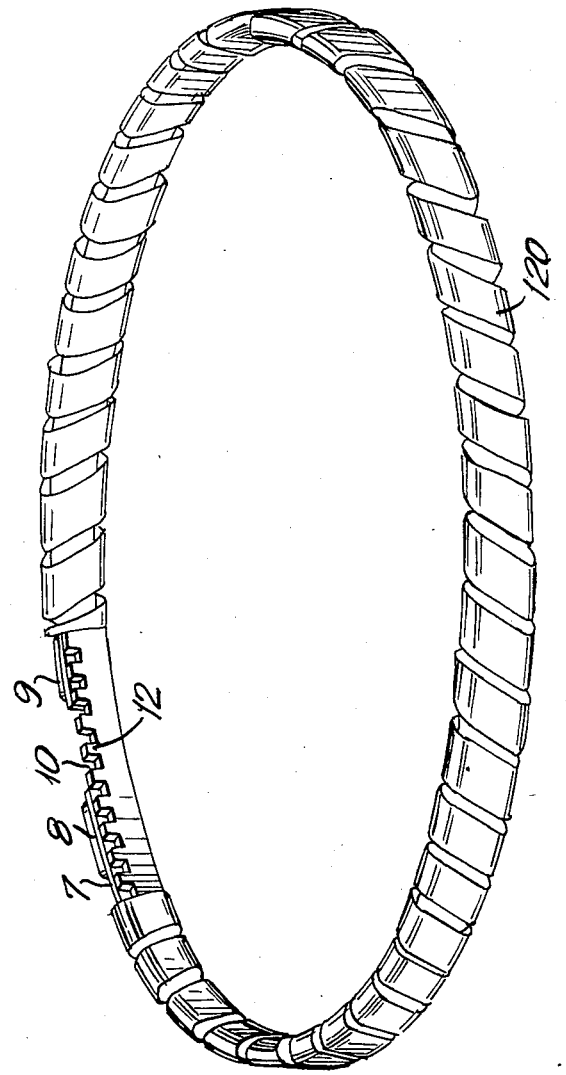
FIG. 11 is a perspective view similar to FIG. 1 of a modified form of ringprosthesis according to the invention utilizing helically wound strips instead of the protective clasps shown in FIG. 2.

It is also possible to provide a helically wound wire or strip, such as the strip 120 shown in FIG. 11, operating as a binding as an alternative for the protective clasps 4, 5 and 6 shown in the drawings. In this case also the textile envelopment of various body tissue compatible materials, such as polyamide, polyester or polytetrafluorine fibers can be provided around the ring. This textile cover can be woven, braided, plaited, or otherwise made into fabric by known processes.

The region 7 of the ringprosthesis which is free of the protective clasps around the coiled spring ribbon is shown in FIG. 3a and the screw guide structure 40 which fits on that portion of the ring is shown with its parts spread out in FIGS. 3b, 3c, 3d and 3e.

Figure 4:
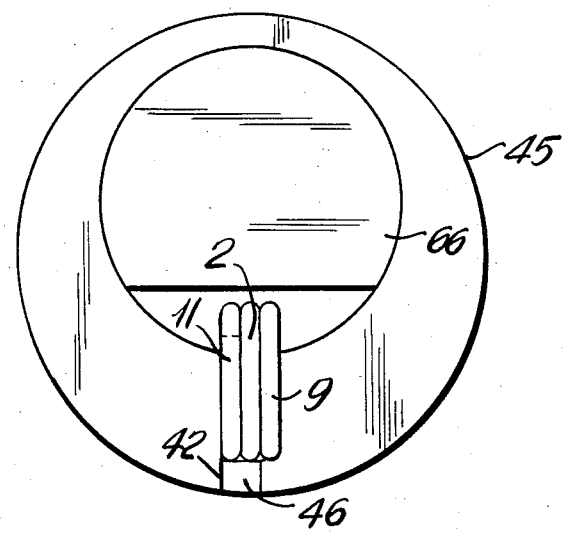
FIG. 4 is a rear elevation view of the guide body mounted on the coiled spring ribbon.

The guide structure 40, as shown particularly in FIGS. 4 and 5, is mounted on the ring 1 between the stop plates 8 and 9. The guide cylinder 44 of the guide structure 40 accordingly has a slot 42 which extends in the axial direction through this entire cylinder 44. The length of the cylinder 44 corresponds substantially to the spacing between the stop plate 8 and 9. In the assembled condition of the ring 1, the upper edge of the spring ribbon 2 lies almost against the inner edge of the slot 42, so that the threads of the screw 15 are in engagement with the toothing 12.

The screw 15, as shown most clearly in FIG. 5, is mounted in a cylindrical hole that passes through the guide cylinder 44. The inner diameter of the hole 43 and the outer diameter of the screw 15 are so determined that the screw 15 is well guided without any risk of jamming in the structure 40, even when large forces are exerted. The threads of the screw 15 are of a size and profile for fitting the toothing 12 of the spring strip, so that an effective conversion of the rotary movement of the screw 15 into a displacement of the coiled second section 11 of the spring ribbon 2 can take place.

The stops 8 and 9 which have the shape of small plates are spot-welded on the outer side of the ring 1, actually on the outer side of the first section of the spring ribbon 2, as can be seen from FIGS. 3a, 4 and 5. In FIG. 5 it can be seen with particular clarity that the cut-out 10 is shorter than the spacing between the stop plates 8 and 9 and that the depth of the cut-out 10 is slightly greater than the depth of the toothing 12.

The cylindrical guide body 44 of the screw guide structure 40 is provided at its end which is shown at the right in FIG. 5 with a ring bead or flange 45. For assembly of the guide structure 40, the cylindrical body 44 having the slot 42 is slipped onto the spring ribbon 2 and then laterally held in position by means of a shell 46, while lengthwise positioning thereof is provided by the stop plates 8 and 9 already mentioned.

The eccentrically located hole 43 in the cylindrical body 44 is closed off by a closure plate 66 at the end of the body 44 where the bead or flange 45 is located. The plate 66 also provides a thrust bearing for the screw 15. At its opposite end, the screw 15 lies against the rim of an orifice 47 through which the point 49 of an adjusting tool 48 shown in FIG. 6c can be introduced for engaging the walls of a square hole 50 in the head of the screw 15 for turning the latter.

Figure 6A:
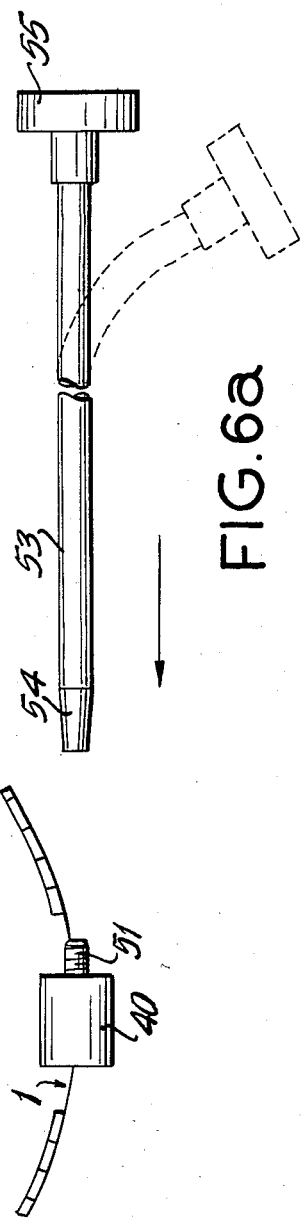
FIG. 6a is a top view of the guide tube approaching the adjusting device of the ringprosthesis.

As can be seen from FIG. 3c and FIG. 5, the insertion orifice 47 is prolonged by a connection piece 51 which is provided with external threads 52 that make it possible to screw, onto the connection piece 51, a guide tube 53 which is shown in FIG. 6a. For this purpose, at the front end of the guide tube 53, internal threads 54 are provided which can either be formed into the end of the tube or provided by an insert (not shown). The opposite end of the guide tube 53 has a holding and twisting grip 55 through which, of course, there is a hole connecting with the inside of the guide tube 53.

FIG. 6a shows the guide tube 53 before it is screwed onto the connection piece 51 of the adjusting device 40.

Figure 6B:
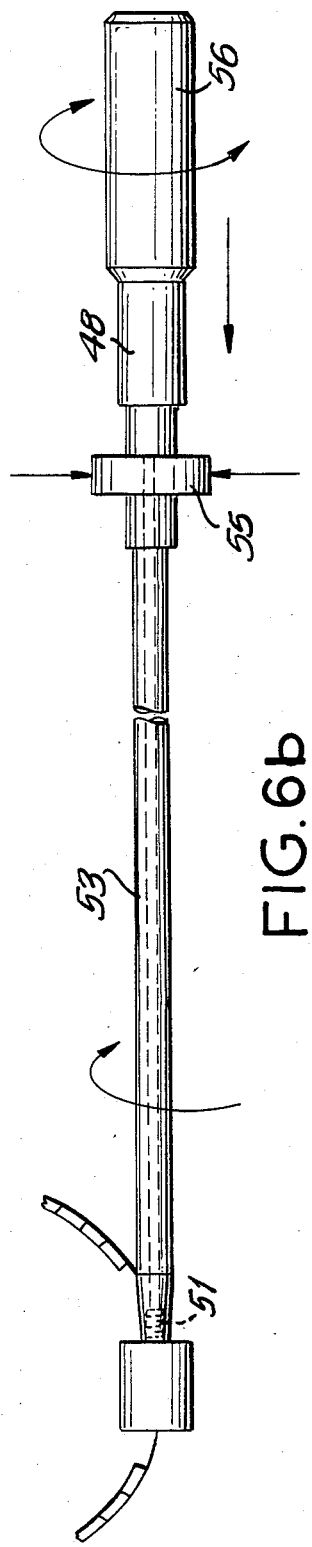
FIG. 6b is a top view of the guide tube connected to the adjusting device and the adjusting tool in place in the guide tube.
Figure 6C:
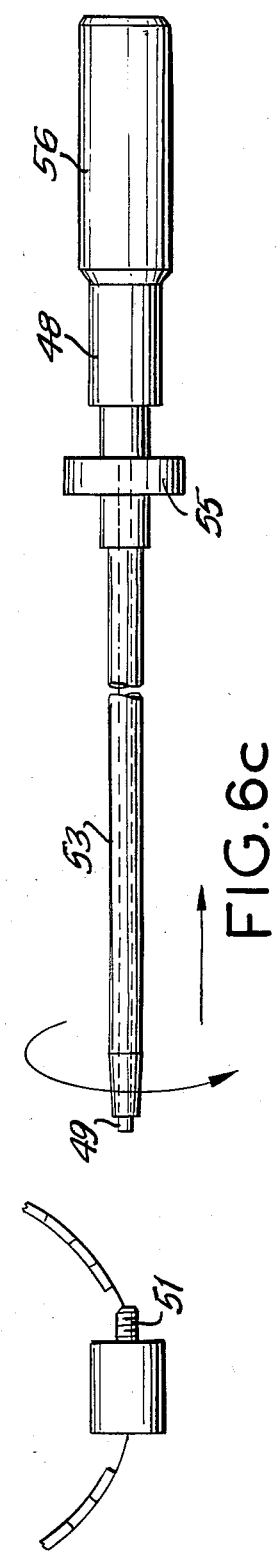
FIG. 6c is a top view showing the adjusting tool and guide tube just after being removed from the adjusting device of the ringprosthesis.

FIG. 6b shows the guide tube screwed onto the connection piece 51 and the adjusting tool 48 inserted into the tube 53, so that the ring 1 can be adjusted by twisting the hand grip 56 of the adjusting tool 48. After setting or adjusting the ring 1, the adjusting tool 48 can be drawn out of the guide tube 53 without unscrewing the tube 53 from the connection piece 51. A further adjustment of the ring 1 is possible by simply introducing the adjusting tool 48 into the tube 53, since the point 49 of the adjusting tool 48 is guided through the guide tube 53 and the connection piece 51 all the way to the square hole 15 of the screwhead. This makes it possible to make fine adjustments, repeated if necessary, after the ring 1 has been implanted in a patient along with the guide tube 53. When the adjustment procedure is finished, the guide tube 53 is unscrewed from the connection piece 51 by twisting the part 55 and then removed.

In the following description, the procedure for implanting the ringprosthesis of the present invention will be illustrated for the case of an implantation in the mitral position. The technique for implantation in the tricuspidal position is similar.

Figure 7:
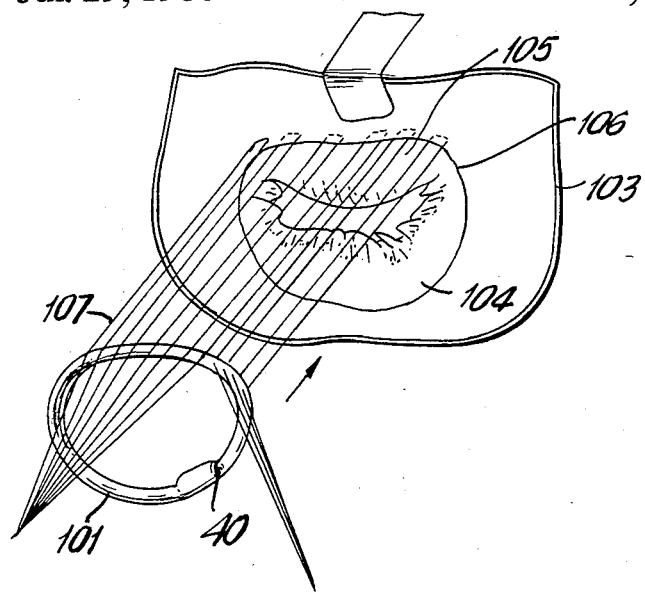
FIG. 7 is a perspective view illustrating attachment of the ringprosthesis to a heart valve by sewing.
Figure 8:
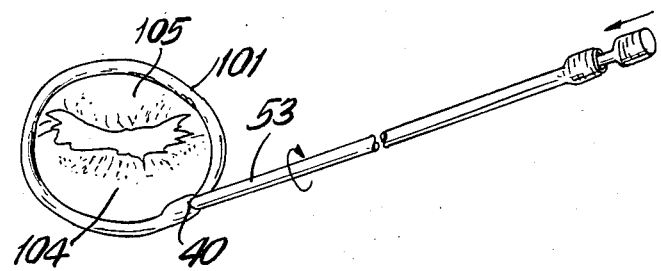
FIG. 8 is a perspective view illustrating the adjustment of the ringprosthesis after it has been implanted.

The patient is first connected to a heart-lung machine and the left auricle 103 is opened up, as shown in FIG. 7. The mitral valve 106 and particularly the forward flap 105 and the rear flap 104 are carefully examined. All necessary plastic reconstructions are then carried out. Thereafter, the adjustable ringprosthesis 101 is assembled by the attachment of the guide tube 53 and the introduction of the adjusting tool 48 therethrough into the guide structure 40, which is shown in FIG. 8 covered over with the synthetic fabric cuff. After checking the operation of its adjustment, the ringprosthesis is put in a middle position of its adjustment and then fastened to the mitral ring, i.e., to the extension of the front and rear flaps of the mitral valve 106, by means of U stitches 107 as shown in FIG. 7. Then the functioning of the diameter adjustment is checked once more by screwing in the guide tube 53 and introduction of the adjustment tool 48. When this test runs positively, the adjustment tool 48 is removed without, however, removing the guide tube 53.

Figure 9:
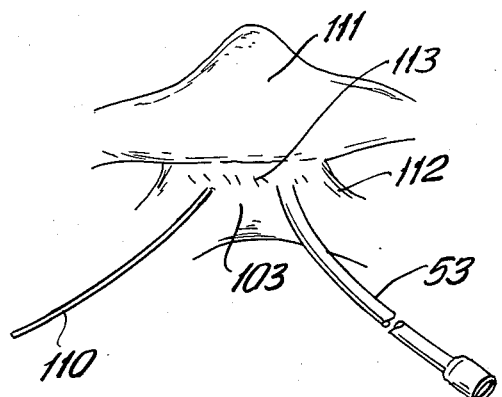
FIG. 9 is a perspective view illustrating the site of the implantation after the removal of a heart-lung machine.

A thin pressure tube 110, the outer end of which is shown in FIG. 9, is introduced into the left auricle for continuous pressure measurement. Both the pressure tube 110 and the guide tube 53 are made to lead out of the patient's body. The left auricle is then closed up by stitches, with both the pressure line 110 and the guide tube 53 being sewed in in the seam 113. FIG. 9 shows the site of the operation after removal of the heat-lung machine. In FIG. 9, there can be recognized in particular the right auricle 111, the left auricle 103, the pulmonary vein 112, the pressure line 110 and the guide tube 53.

When the operation has proceeded that far, the heart is given time for stabilization, which requires about thirty minutes. Thereafter, the adjusting tool 48 is introduced through the guiding tube 53 and the actual adjustment of the ringprosthesis is carried out with the heart beating and with blood circulation proceeding under stable conditions. In this procedure, the ring 1 is first expanded far enough for typical signs of insufficiency to appear in the continuously registered pressure curve of the left auricle 103, i.e., signs of a leaky valve. The ring 1 is then reduced in size by twisting the adjusting tool in the opposite direction until typical signs of valve stenosis appear, i.e., a valve that is too narrow. The number of turns of the adjustment tool 48 necessary for going from insufficiency to stenosis is counted in this operation. Thereafter the ring 1 is again widened, this time, however, to a midposition between the two extremes just mentioned. The pressure curve which can be observed on a monitor serves continuously for checking what is going on. This curve must be normal, both with regard to its overall height and also with regard to its contour.

Figure 10:
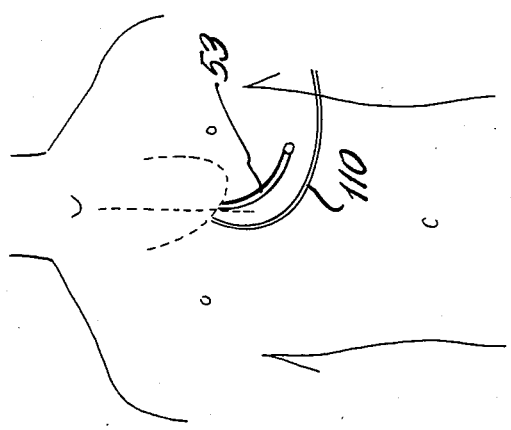
FIG. 10 is a front view of a patient's chest after closure of the wound, showing a pressure line and the guide tube of the ringprosthesis protruding from his body.

Finally, the adjusting tool 48 is removed, and the chest of the patient is closed while leaving both the pressure line 110 and also the guide tube 53 in place and leading outwards. This is shown in FIG. 10. It can be seen from FIG. 10 how the guide tube 53 lies on the patient's chest and how the pressure line 110 leads away to an electronic manometer not shown in the drawing.

During some hours following an operation such as described, there occurs a further healing and recovery of the heart, and its pumping power increases. This means that with the same mitral valve opening more blood now flows than at the time when the patient was still in the operating room where the original adjustment of the ringprosthesis was performed. The ring size that was optimal under those conditions is now usually no longer optimal. Renewed adjustment is necessary in order to take account of the changed conditions. For this reason a final adjustment is not carried out until a few hours after the operation. Thereafter, the guide tube 53 is released from the coupling piece 51 by counter-clockwise rotation about its axis and then removed by a light pull. The pressure line 110 is correspondingly removed.

The ringprosthesis described with reference to FIGS. 1–6c, in addition to being useful for correction of insufficiencies of the mitral valve or of the tricuspidal valve, can also be used for constriction of the pulmonal artery. This provides the possibility of controlling the throttling of the pulmonal artery from outside the patient's body. In this manner, an initially mild constriction provided on the operating table can be made more pronounced after the heart has become used to it.

The ringprosthesis of the present invention lends itself well to experimental uses, since the ringprosthesis of this invention, while indeed flexible, is at the same time elastic. Accordingly, after an implantation in an experimental animal, it becomes possible to produce in a manner reproducible at any time, an insufficiency or a stenosis of various degrees and to vary that from the outside. Insufficiency and stenosis and their effect on circulation, on the heart and on the lungs, can be investigated with precision in this way. Furthermore, the ring can be applied to the lower vena cava and then throttled down by control from the outside to such an extent that the return flow to the heart is reduced and a shock condition arises. In that way it is possible to develop a shock model that is reproducible and reversible at any time.

Although the invention has been described with reference to a particular illustrative embodiment, it will be understood that variations and modifications are possible within the inventive concept.

We claim:

1. Adjustable ringprosthesis for surgical correction of heart valve malfunction comprising:

a tubular plastic sleeve capable of being sewn into a heat valve ring of the mitral or the tricuspidal valve;

a spring ribbon coiled within said sleeve to form a ring and having an end coiled internally in the ring which end has a toothed edge and is circumferentially shiftable;

an adjusting device for shifting said shiftable spring end, mounted on the externally coiled part of said ribbon astride an edge thereof, into which device the forward end of an adjusting tool can be inserted and having a screw rotatably held for being turned by said adjusting tool in a screw guide structure mountable astride an edge of said spring ribbon and having a guide orifice for introduction of a screw-driving tool, and in which device said internally coiled end of said spring ribbon engages said toothed edge into the threads of said screw;

a connection piece (51) extending in tubular fashion from said screw guide structure so as to extend said guide orifice (47) thereof and having a configuration for detachable coupling with a guide tube (53) for the introduction of said adjusting tool (48), said screw guide structure having a slot into which said toothed edge of said spring ribbon enters and through which said screw has engagement with said toothed edge of said spring ribbon, and a thrust bearing (66) for said screw (15) provided in said screw guide structure in the end thereof opposite said guide orifice (47).

2. Ringprosthesis according to claim 1, in which said connection piece (51) is constituted as a tubular nipple having external threading (52).

3. Ringprosthesis according to claim 1, in which said guide structure (40) comprises a cylindrical body (44) having an eccentrically located cavity (43) for said screw (15), said slot (42) being provided in said cylindrical body, extending outward from said cavity to the periphery of said cylindrical body (44) in a place at which, by reason of said eccentric location, the wall of said cavity (43) provided by said cylindrical body is relatively thick.

4. Ringprosthesis according to claim 3, in which said slot (42) in said cylindrical body (44) is located where the thickness of said cavity wall is at a maximum.

5. Ringprosthesis according to claim 3, in which said cylindrical body (44) has a protruding annular bead (45) at one end of said body.

6. Ringprosthesis according to claim 5, in which said screw guiding structure (40) includes a shell surrounding said cylindrical body (44), abutting said annular bead (45), and also encircling said coiled spring ribbon (2, 11) for holding said screw guiding structure (40) on said coiled spring ribbon.

7. Ringprosthesis according to claim 6, in which said cylindrical body (44) is so constituted as to be fastenable on said spring ribbon by being pushed thereon and then be held in place by means of said shell (46) and two laterally disposed stop plates (8, 9) attached to said spring ribbon (2).

8. Ringprosthesis according to claim 1, in combination with a said guide tube (53) capable of being coupled to said connection piece (51) and having an internally threaded (54) forward end and a rear end equipped with a turning and holding part (55), whereby said adjusting tool (48), when constituted as a screwdriver which is rigid with respect to rotation, is introduced by one end (29) thereof, which is capable of being inserted in a tool engagement location (50) provided in said screw (15) in a manner rigid with respect to rotation.

9. Combination according to claim 8, in which said guide tube (53) is flexible.

10. Ringprosthesis according to claim 1, in which said spring ribbon (2) is bound by at least one helically wound strip for holding overlapping parts of said ribbon together to form a ring in a manner permitting ring diameter changes by operation of said adjusting device and relative slippage of overlapping portions of said spring strip.

11. Ringprosthesis according to claim 1, in which said spring ribbon (2) has segments of different flexibility such that an adjustment of said ringprosthesis by means of said adjusting device is usable to produce a deformation of the ring shape deviating from circularity.

* * * * *